US006444001B1

United States Patent
Sheffield

(10) Patent No.: US 6,444,001 B1
(45) Date of Patent: Sep. 3, 2002

(54) SEPARATOR AND SEPARATOR SYSTEM

(76) Inventor: Glenn E. Sheffield, 2009 19th Ave. North, Texas City, TX (US) 77590

(*) Notice: Subject to any disclaimer, the term of this patent is extended or adjusted under 35 U.S.C. 154(b) by 0 days.

(21) Appl. No.: 09/524,732

(22) Filed: Mar. 14, 2000

(51) Int. Cl.$^7$ .......................... B01D 45/02; B01D 50/00
(52) U.S. Cl. .......................... 55/342; 55/320; 55/322; 55/326; 55/441; 55/DIG. 17; 55/482; 55/319; 96/413; 73/863.21
(58) Field of Search .......................... 96/413, 417, 191, 96/192; 55/320, 321, 322, 323, 326, 342, 421, DIG. 25, 318, 319, 434, 442, 465, 482, DIG. 17, 441; 95/273; 73/863.21, 863.23, 28.04

(56) References Cited

U.S. PATENT DOCUMENTS

| | | | | |
|---|---|---|---|---|
| 2,489,893 A | * | 11/1949 | Johnson .................... | 73/863.21 |
| 3,557,869 A | * | 1/1971 | Kriftel et al. ............ | 73/863.21 |
| 3,678,661 A | * | 7/1972 | Davis ........................... | 55/322 |
| 3,970,428 A | * | 7/1976 | Barringer ................. | 73/863.21 |
| 4,791,820 A | * | 12/1988 | Lawrence et al. ........ | 73/863.21 |
| 5,423,228 A | * | 6/1995 | Budd et al. .............. | 73/863.21 |
| 5,783,756 A | * | 7/1998 | Xiong et al. ............. | 73/863.23 |

OTHER PUBLICATIONS

Clevett, Kenneth J., Process Analyzer Technology, Preface and pp. 808–809. John Wiley & Sons, Inc., 1986.
Flier: "Hi–eF Liquid/Gas Separators." Anderson Separator Company, Strongsville, Ohio. Admitted prior art.
Flier: "AVS Series Vane Separators," Anderson Separator Company, Strongsville, Ohio. Admitted prior art.
Flier: "AVGS Series Vertical Gas," Anderson Separator Company, Strongsville, Ohio. Admitted prior art.
Flier: "AFS Series Filter." Anderson Separator Company, Strongsville, Ohio. Admitted prior art.
Flier: "ACF Series Coalescer Filter." Anderson Separator Company, Strongsville, Ohio. Admitted prior art.
Flier: "Line Type Models: L, LC, LCF, LCR, LCC, LCCR Separators." Anderson Separator Company, Strongsville, Ohio. Admitted prior art.
Flier: "CL Series Coalescing Separator," Anderson Separator Company, Strongsville, Ohio. Admitted prior art.
Flier: "Internal Type IM and ID Hi–eF Separators." Anderson Separator Company, Strongsville, Ohio. Admitted prior art.
Flier: "Combination Separator–Trap HSW Series 300 PSIG." Anderson Separator Company, Strongsville, Ohio. Admitted prior art.
See paragraph 3 of Information Disclosure Statement. Admitted prior art.

* cited by examiner

Primary Examiner—Duane Smith
Assistant Examiner—Jason M. Greene
(74) Attorney, Agent, or Firm—Browning Bushman P.C.

(57) ABSTRACT

A separator for separating a first fluidized component from a second fluidized component, the separator having a monolithic body with first and second, generally vertically disposed, elongate chambers, each of the chambers having a lower end and an upper end, each of the chambers having a first outlet disposed generally at the lower end and a second outlet disposed generally at the upper end, each of the chambers having an inlet that feeds a fluid stream toward the lower end of the chamber, a fraction of the gas entering the first chamber supplying the feed stream to the second chamber.

20 Claims, 3 Drawing Sheets

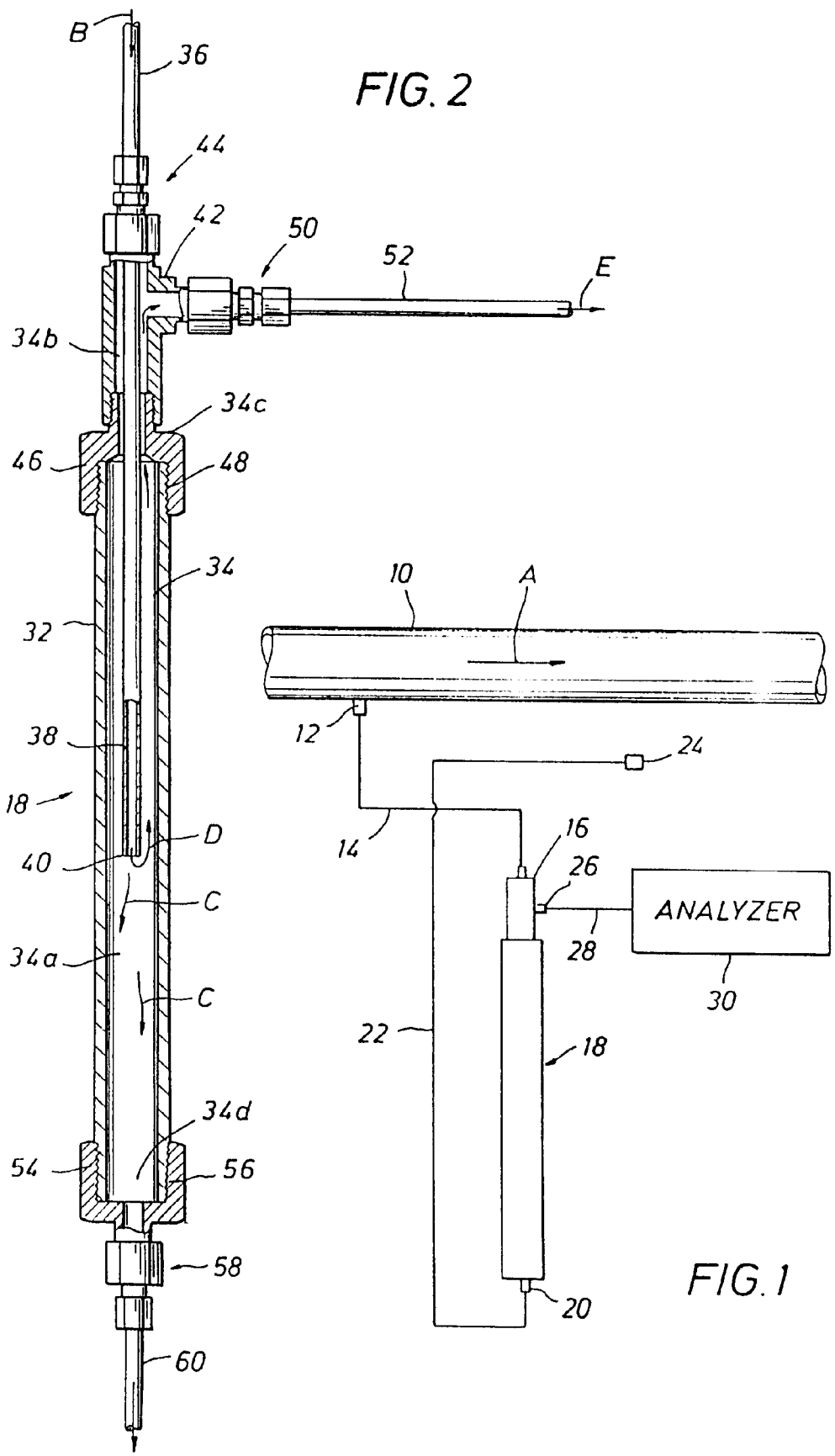

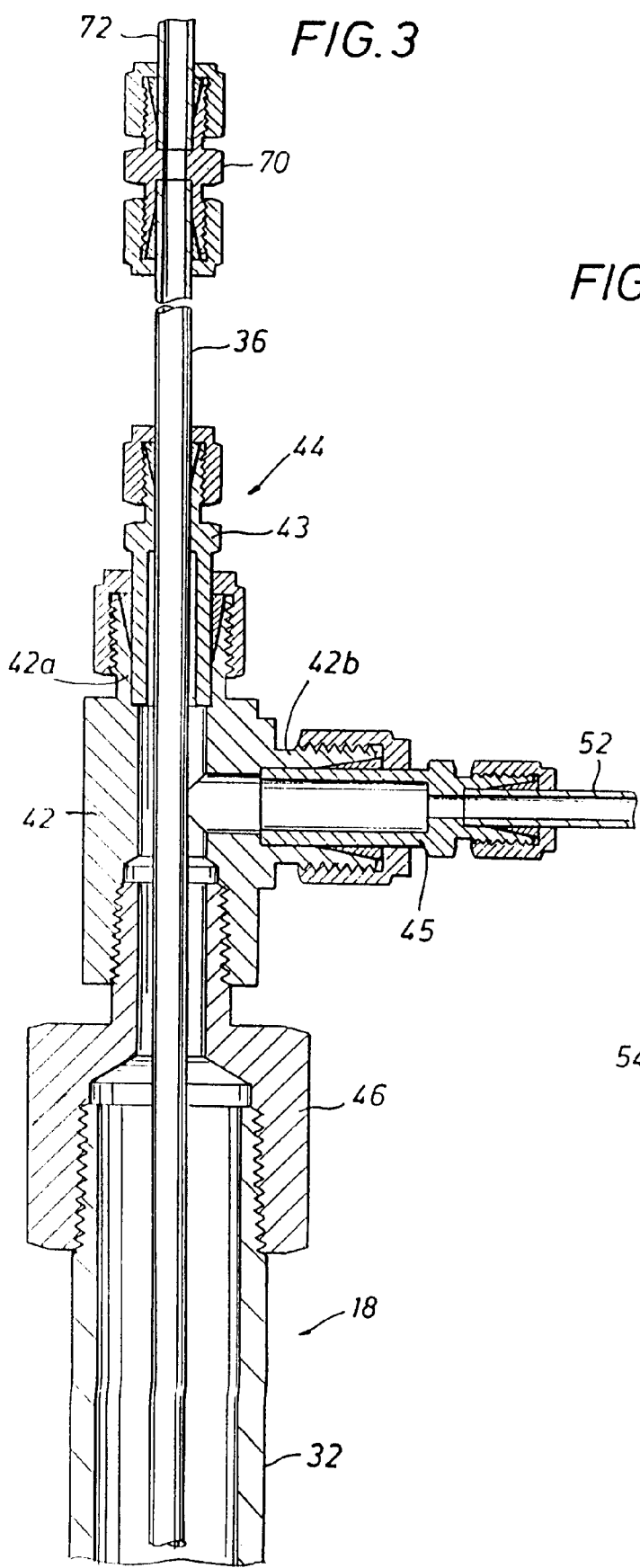
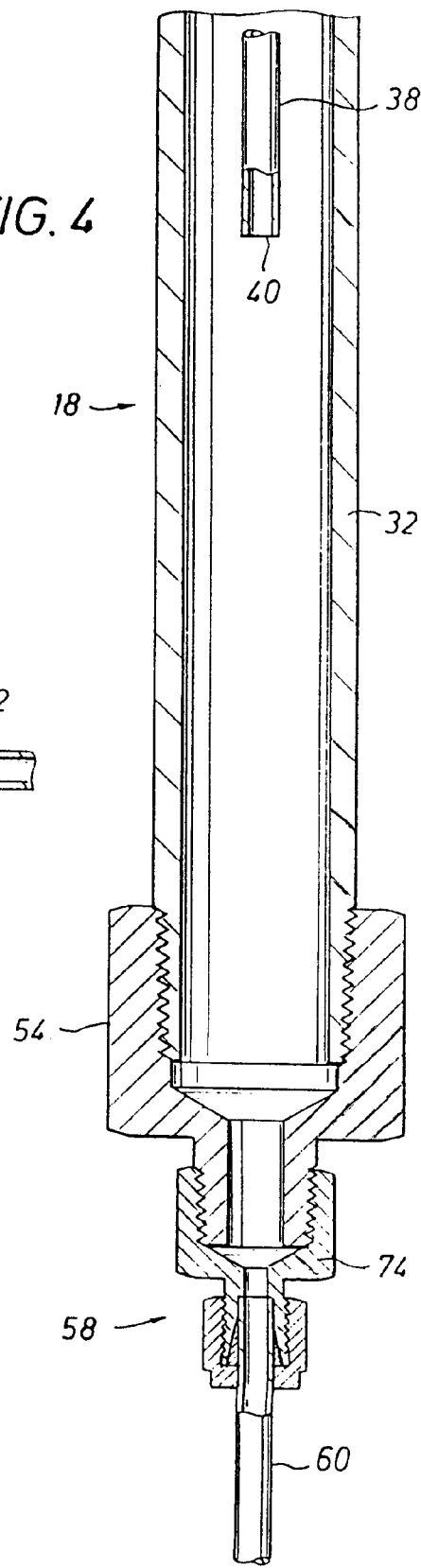

SEPARATOR AND SEPARATOR SYSTEM

BACKGROUND OF THE INVENTION

1. Field of the Invention

The present invention relates to separators for separating fluidized components of a process fluid and to a system for separating components present in a high pressure process fluid.

2. Description of the Prior Art

In many chemical and refining processes, it is necessary to analyze a process stream. Typically, this is done by removing a slip stream from the process stream and passing the slip stream through an analyzer. Frequently, it is necessary that the process stream to be analyzed be freed of certain components for the analysis to be accurate. For example, in analyzing gas streams such as hydrogen, which is widely used in refinery operations, it is necessary that the hydrogen stream be freed of any particulates and/or water prior to being sent to the analyzer. To accomplish drying the gas stream, e.g., a hydrogen stream, it is common to pass the slip stream through a separator that removes particulates and/or water and produces a separated portion of the process stream that is substantially dry.

SUMMARY OF THE INVENTION

It is therefore an object of the present invention to provide a system for separating a first fluidized component from a second fluidized component wherein the source of the fluidized components is at a high pressure—i.e., of at least 80 psi.

Another object of the present invention is to provide a compact separator that is relatively small in size and requires a minimum amount of plumbing.

The above and other objects of the present invention will become apparent from the drawings, the description herein, and the appended claims.

In accordance with one aspect of the present invention, there is provided a system for separating a first fluidized component from a second fluidized component. The system of the present invention comprises a source of process fluid that contains the first and second fluidized components, the process fluid being at a pressure of at least 80 psi. The system includes a separator that has an inlet, a first outlet for removing a first separated portion of the process fluid, and a second outlet for removing a second separated portion of the process fluid. The separator includes a housing that defines a generally vertically disposed, elongate chamber. The chamber has a lower end and an upper end, the first outlet being disposed generally at the lower end of the chamber, the second outlet being disposed generally at the upper end of the chamber. The inlet is connected to the source of process fluid and includes a tube having an open end received in the chamber. The tube serves to direct the process fluid entering the chamber toward the lower end of the chamber.

In another embodiment of the present invention, there is provided a separator for separating a first fluidized component from a second fluidized component. The separator includes a monolithic body defining first and second generally vertically disposed, elongate chambers. Each of the chambers has a lower end and an upper end. The first chamber has first and second, first chamber outlets, the first first chamber outlet being disposed generally at the lower end of the first chamber, the second first chamber outlet being generally disposed at the upper end of the first chamber. The second chamber likewise has first and second second chamber outlets, the first second chamber outlet being disposed generally at the lower end of the second chamber, the second second chamber outlet being disposed generally at the upper end of the second chamber. There is a first chamber inlet into the first chamber that includes a first tube having an open end received in the first chamber, the first tube serving to direct a process fluid entering the first chamber toward the lower end of the first chamber. There is a second chamber inlet into the second chamber, the second chamber inlet including a second tube having an open end received in the second chamber. The second chamber inlet is in open communication with the second first chamber outlet. The second tube in the second chamber serves to direct separated process fluid from the first chamber that is entering the second chamber toward the lower end of the second chamber.

BRIEF DESCRIPTION OF THE DRAWINGS

FIG. 1 is a schematic view showing the system of the present invention with reference to a high pressure source of process fluid;

FIG. 2 is an elevational view, partly in section, showing the separator used in the system of FIG. 1;

FIG. 3 is an enlarged, elevational view, partly in section, showing the upper end of the separator shown in FIG. 2;

FIG. 4 is an enlarged, elevational view, partly in section, showing the lower end of the separator shown in FIG. 2.

DESCRIPTION OF THE PREFERRED EMBODIMENTS

Figure 5:
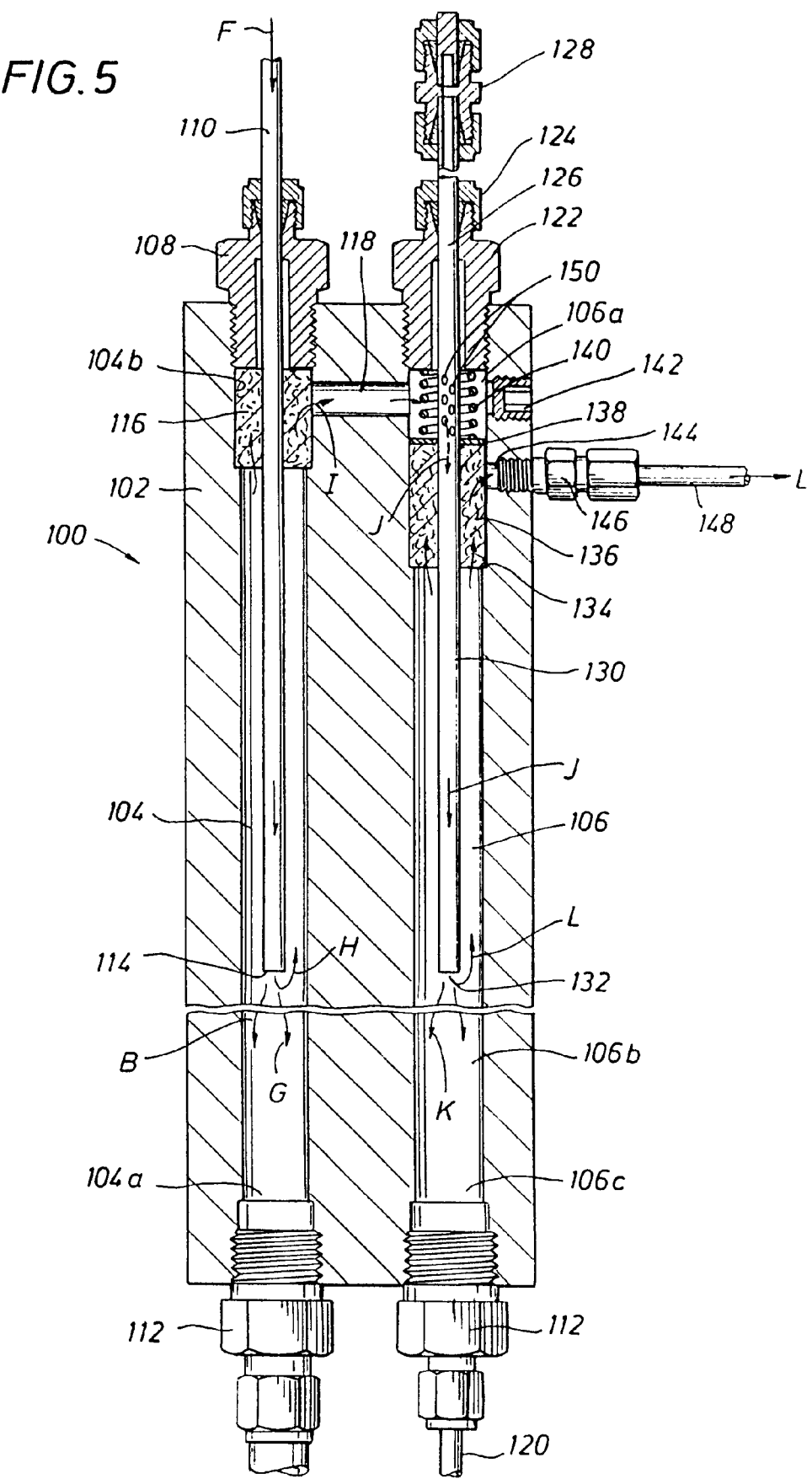
FIG. 5 is an elevational view, partly in section, of another embodiment of a separator according to the present invention.

While the invention will be described with particular reference to a separator for use in an analyzer train, it is to be understood that the separator and separator system of the present invention can be employed as a process scale separator/separator system forming part of a processing train wherein it is desired to effect separation of a first fluidized component from a second fluidized component present in a process fluid.

With reference first to FIG. 1, there is shown a schematic of an analyzer train used to analyze a process stream under high pressures—i.e., 80 psi or more. A flow line 10 contains a high pressure source of fluid, which can be liquid but more generally is gaseous in nature, flowing in the direction of arrow A. It will be understood that the process fluid in line 10 contains two or more components that are fluidized in the sense that whether one or more of the components is a solid or liquid entrained in one or more other components that are gases or liquids, the components are all fluidized in the sense that they are dispersed in the fluid phase. A slip stream of the process fluid in line 10 is removed via a tap 12 and passed via a line 14 to the inlet 16 of a separator shown generally as 18 and described more fully hereinafter. A first separated component of the process stream entering separator 18 is removed via a first outlet 20 and returned via a line 22 to the process at a lower pressure tap 24. A second fluidized component separated from the process stream entering separator 18 is removed via a second outlet 26 and transferred via a line 28 to an analyzer 30.

By way of example, assuming that the process fluid in flow line 10 is a high pressure (e.g., 350 psi) wet hydrogen stream, a slip stream of the wet hydrogen stream is removed via tap 12 and line 14 and introduced into separator 18, where it is separated to provide a first fluidized component, e.g., a hydrogen stream substantially freed of any solid particulates, water, or other entrained liquids that is passed via outlet 26 and line 28 to analyzer 30. The remainder of the process stream comprising the second fluidized component less a small amount of hydrogen that has been transferred to the analyzer 30 is removed from separator 18 via line 20 and returned via second tap 24 to a lower pressure point (e.g., 150 psi) in the process.

Reference is now made to FIGS. 2, 3, and 4 for a detailed description of an embodiment of the separator 18. Separator 18 comprises a generally cylindrical housing 32, forming an internal, generally elongate, cylindrical chamber 34. Chamber 34 has a lower portion 34a and an upper portion 34b, portion 34b having a smaller diameter than portion 34a. A passageway 34c connects upper portion 34b and lower portion 34a of chamber 34. A tube 36 has a portion 38 received in lower portion 34a of chamber 34, tube 36 being provided with an open end 40. Tube 36 is connected to a T-fitting 42 by a coupling assembly shown generally as 44 and described more fully hereinafter. T-fitting 42 forms the upper portion 34b of chamber 34 and is threadedly received to a union 46 that is threadedly received as at 48 to the threaded, upper end of housing 32. Housing 32 is also threaded at its lower end, the threaded lower end 54 being threadedly attached to a second union 56, which in turn is attached by a coupling assembly 58 to an outlet tube 60.

In operation, a process gas enters tube 36 in the direction shown by arrow B and exits open end 40, open end 40 serving to direct the flow of the process fluid in the direction of arrows C—i.e., toward the bottom 34d of chamber 34 toward the outlet formed by tube 60, tubes 36 and 60 being generally coaxially aligned. A portion of the process fluid exiting open end 40 moves up chamber 34 in the direction of arrow D, passes through restriction 34c into upper portion 34b of chamber 34, and exits outlet tube 52 in the direction of arrow E.

In a specific embodiment, separator 18 is constructed of all stainless steel components, housing 32 being formed of a threaded pipe 12" long and having a 1" diameter. As shown in FIG. 3, union 46 is a 1" pipe to ½" pipe threaded connection, which is connected to T-fitting 42, which in turn is provided with ½" tubing fittings 42a and 42b. Fitting 42a is connected to reducer tubing fitting 43 (½" to ¼") for receipt of tubing 36. A coupling 70 provided with tubing fittings can be used to couple tubing 36 to another section of tubing 72 and then to line 14 (FIG. 1). Likewise, tubing fitting 42b is connected to tubing reducer 45 (½" to ¼") to accommodate outlet tubing 52, which is connected to line 28 (FIG. 1). Tubing 36 is ¼" tubing that extends approximately halfway down the length of housing 32. Union 54 is like union 46, a 1" to ½" threaded pipe connection, which in turn is connected to a ½" pipe to ¼" tubing fitting 74, outlet tubing 60 being received therein.

With reference now to FIG. 5, there is shown another embodiment of a separator in accordance with the present invention. Separator 100 shown in FIG. 5 is comprised of a monolithic body 102 defining a first, generally cylindrical chamber 104 and a second, generally cylindrical chamber 106, chambers 104 and 106 being generally vertical. Chamber 104 has a lower end 104a and an upper end 104b. In the embodiment shown in FIG. 5, chamber 106 is divided into an upper portion 106a and a lower portion 106b, lower portion 106b having a lower end 106c.

Threadedly received in the upper end of chamber 104 is a pipe-to-tubing union 108 through which is received a tube 110. At the lower end of chamber 104, there is threadedly received a pipe-to-tubing fitting 112. Tubing 110 is sealingly held in union 108 and terminates in chamber 104 in an open end 114. As seen, open end 114 of tubing 110 and the outlet formed by union 112 are generally coaxial. At the upper end 104b of chamber 104, there is a filter 116 disposed in surrounding relationship to tube 110. Filter 116 can be made from a wide variety of materials, e.g., metallic meshes such as stainless steel mesh. Filter 116 overlies one end of a passageway 118, passageway 118 being in open communication with chamber 104.

Chamber 106 has an outlet located at lower end 106c, the outlet being formed by a union 112, which receives a piece of outlet tubing 120. The upper end of chamber 106 threadedly receives a union 122 having a tubing connection shown generally as 124 through which a piece of tubing 126 extends. Tubing 126 is in turn plugged exteriorally of housing 102 by a tubing plug shown generally as 128. Tubing 126 has a portion 130 that extends into chamber 106 and terminates in an open end 132, open 132 being generally coaxial with the outlet formed by union 112. As can be seen, chambers 104 and 106 and tubing 110 and 126 are generally cylindrical in nature.

Chamber 106 has an annular shoulder 134 upon which rests a filter 136, which can be similar in makeup to filter 116. A seal washer 138 rests atop filter 136 and is held against shoulder 134 by means of a spring 140 that is held between union 122 and seal washer 138. It can thus be seen that filter washer 138 effectively divides and seals off the lower portion 106b of chamber 106 from the upper portion 106a of chamber 106. A threaded plug 142 is received in a construction hole that allows drilling of passageway 118. A second outlet from chamber 106 is provided by port 144, in which is received a threaded connector 146, in which is received a piece of outlet tubing 148.

The portion of tube 126 that extends through the upper portion 106a of chamber 106 is provided with a series of ports 150, ports 150 providing open communication between upper portion 106a of chamber 106 and the interior of tube 126.

In operation, the fluid stream enters tube 110 in the direction of arrow F and exits into chamber 104 through open end 114, the bulk of the fluid being directed toward lower end 104a in the direction of arrows G. A portion of the fluid moves in the direction of arrow H up the annulus between tube 110 and the walls forming chamber 104. The fluid moving up the annulus passes through filter 116 and enters passageway 118 in the direction shown by arrow I. Fluid then flows into the upper portion 106a of chamber 106 through the ports 150, down tube 126 in the direction of arrow J, exiting the open end 132 of tube 126, where it is directed toward the bottom 106c of chamber 106 in the direction of arrows K. A portion of the fluid flows upwardly in the direction of arrow L in the annulus formed between the walls forming chamber 106 and tube 126, that portion of the fluid passing through filter 136 into passage 144, then through the outlet formed by fitting 146.

Separators 18 and 100 operate primarily by virtue of momentum and gravity. For example, in the case where the process stream being fed to the separators is a gas-liquid mixture, e.g., a wet hydrogen stream, momentum coupled with the force of gravity forces the heavier water droplets or aerosol toward the bottom ends of the chambers out through the bottom outlets. In contrast, the lighter gas flows upward through the annulus between the tube and the housing and exits at the upper outlet(s), where it can then be sent directly to an analyzer. With respect to separator 100, the filters 116 and 136 actually act as mist-catchers or coalescers for any contaminants that are not discharged through the outlets at the bottom ends of the chambers.

It will be appreciated that the separators or, more particularly, the chambers in the separators are disposed in a generally vertical position. This does not necessitate that the chambers be exactly vertical but only that they be positioned such that heavier contaminants are forced by gravity toward the lower ends of the chambers. Also, any accumulation of water or other contaminants separated in the chambers will pass through the lower outlets or drains.

A unique feature of the separation system of the present invention for use with high pressure fluid sources, e.g., 80 psi or more, resides in the fact that fluid flow through the separator is quite rapid; i.e., as the process fluid exits the open end of the tube in the chamber, it is directed toward and out the outlet at the bottom of the chamber so that there is no interruption of flow. Thus, the heavier material(s), having much greater momentum, continue to move toward the outlets at the bottom of the chamber, whereas the lighter components, having significantly less momentum, are allowed to pass upwardly through the chamber in the annulus between the tube and the chamber walls to exit the outlet at the upper part of the chamber. In other words, there is an uninterrupted flow path from the tube to the outlet at the bottom of the chamber. As the process fluid enters the chamber from the open end of the tube, there is a loss in velocity. This loss in velocity results in the loss of momentum of both the heavier and lighter particles, e.g., the gases and the aerosol. However, the heavier materials still possess sufficient momentum such that they, for the most part, continue to travel through the outlet at the bottom of the chambers. The loss of momentum in the lighter materials, e.g., the gases, allows at least some of the gas to travel up the annulus between the tube and the chamber walls and exit the outlet at the upper part of the chamber.

While the kinetic separators of the present invention find particular application in separating entrained water either in the form of mist, aerosols, or the like from gas streams such as hydrogen, the separators can also be employed to separate solid particulates that may be entrained in the gas stream. Additionally, the separators can be employed to separate one immiscible liquid from a second immiscible liquid, e.g., water from a hydrocarbon stream wherein the hydrocarbon stream, e.g., gasoline, is the continuous phase and the water forms the heavier discontinuous phase.

The foregoing description and examples illustrate selected embodiments of the present invention. In light thereof, variations and modifications will be suggested to one skilled in the art, all of which are in the spirit and purview of this invention.

What is claimed is:

1. A separator for separating a first fluidized component from a second fluidized component, comprising:

a monolithic body, said monolithic body defining first and second generally vertically disposed, elongate chambers;

each of said chambers having a lower end and an upper end;

said first chamber having first and second first chamber outlets, said first first chamber outlet being disposed generally at said lower end of said first chamber, said second first chamber outlet being disposed generally at the upper end of said first chamber, said second chamber having first and second second chamber outlets, said first second chamber outlet being disposed generally at said lower end of said second chamber, said second second chamber outlet being disposed generally at said upper end of said second chamber, said second chamber including an upper portion and a lower portion, said upper portion being in open communication with said second first chamber outlet;

a first chamber inlet into said first chamber, said first chamber inlet including a first tube having an open end received in said first chamber, said first tube serving to direct a process fluid entering said first chamber toward said lower end of said first chamber;

a second chamber inlet into said second chamber, said second chamber inlet including a second tube having an open end received in said second chamber, said second chamber inlet being in open communication with said second first chamber outlet, said second tube serving to direct separated process fluid from said first chamber toward said lower end of said second chamber; and a seal between said upper portion of said second chamber and said lower portion of said second chamber, said second tube having a lower portion received in said lower portion of said second chamber, and an upper portion received in said upper portion of said second chamber and having a plurality of ports communicating with the interior of said second tube.

2. The separator of claim 1 wherein said first first chamber outlet and said open end of said first tube are generally coaxial.

3. The separator of claim 1 wherein a first filter is disposed in said first chamber in surrounding relationship to said tube and overlying said second first chamber outlet.

4. The separator of claim 1 wherein said second first chamber outlet and said second chamber inlet are formed by a common passageway.

5. The separator of claim 1 wherein said open end of said second tube and said first second chamber outlet are substantially coaxial.

6. The separator of claim 1 including a filter in surrounding relationship to said second tube and overlying said second second chamber outlet.

7. The separator of claim 1 wherein there is a filter in said lower portion of said second chamber, said second second chamber outlet being in open communication with said lower portion of said second chamber, said filter overlying said second second chamber outlet.

8. A separator for separating a first fluidized component from a second fluidized component, comprising:

a body defining first and second generally vertically disposed, elongate chambers;

each of said chambers having a lower end and an upper end;

said first chamber having first and second first chamber outlets, said first first chamber outlet being disposed generally at said lower end of said first chamber, said second first chamber outlet being disposed generally at the upper end of said first chamber, said second chamber having first and second second chamber outlets, said first second chamber outlet being disposed generally at said lower end of said second chamber, said second second chamber outlet being disposed generally at said upper end of said second chamber, said second chamber including an upper portion in fluid communication with said second first chamber outlet;

a first chamber inlet into said first chamber, said first chamber inlet including a first tube having an open end received in said first chamber, said first tube serving to direct a process fluid entering said first chamber toward said lower end of said first chamber;

a second chamber inlet into said second chamber, said second chamber inlet including a second tube having an open end received in said second chamber, said second chamber inlet being in open communication with said second first chamber outlet, said second tube serving to direct separated process fluid from said first chamber toward said lower end of said second chamber;

a seal surrounding said second tube and fluidly separating said upper portion of said second chamber from said lower portion of said second chamber; and a connecting passageway within said body fluidly connecting said second first chamber outlet and said upper portion of said second chamber.

9. The separator of claim 8 wherein said first first chamber outlet and said open end of said first tube are generally coaxial.

10. The separator of claim 8, further comprising:

a first filter is disposed in said first chamber in surrounding relationship to said tube and overlying said second first chamber outlet.

11. The separator of claim 8 wherein said connecting passageway is a generally horizontal passageway.

12. The separator of claim 8 wherein said open end of said second tube and said first second chamber outlet are substantially coaxial.

13. The separator of claim 8, further comprising:

a filter in surrounding relationship to said second tube and overlying said second second chamber outlet.

14. The separator of claim 8 further comprising:

a filter in said lower portion of said second chamber, said second second chamber outlet being in open communication with said lower portion of said second chamber, said filter overlying said second second chamber outlet.

15. The separator of claim 8 wherein said second tube includes a plurality of ports communicating with the interior of said second tube.

16. A separator for separating a first fluidized component from a second fluidized component, comprising:

a body defining first and second generally vertically disposed, elongate chambers;

each of said chambers having a lower end and an upper end;

said first chamber having first and second first chamber outlets, said first first chamber outlet being disposed generally at said lower end of said first chamber, said second first chamber outlet being disposed generally at the upper end of said first chamber, said second chamber having first and second second chamber outlets, said first second chamber outlet being disposed generally at said lower end of said second chamber, said second second chamber outlet being disposed generally at said upper end of said second chamber, said second chamber including an upper portion in fluid communication with said second first chamber outlet;

a first chamber inlet into said first chamber, said first chamber inlet including a first tube having an open end received in said first chamber, said first tube serving to direct a process fluid entering said first chamber toward said lower end of said first chamber;

a second chamber inlet into said second chamber, said second chamber inlet including a second tube having an open end received in said second chamber, said second chamber inlet being in open communication with said second first chamber outlet, said second tube serving to direct separated process fluid from said first chamber toward said lower end of said second chamber;

a seal surrounding said second tube and fluidly separating said upper portion of said second chamber from said lower portion of said second chamber; and a connecting passageway within said body fluids connecting said second first chamber outlet and said upper portion of said second chamber;

a first filter disposed in said first chamber in surrounding relationship to said first tube and overlying said second first chamber outlet; and a second filter in surrounding relationship to said second tube and overlying said second second chamber outlet.

17. The separator of claim 16 wherein said second filter is disposed in said lower portion of said second chamber, said second second chamber outlet being in open communication with said lower portion of said second chamber.

18. The separator of claim 16 wherein said first first chamber out let and said open end of said first tube are generally coaxial.

19. The separator of claim 16 wherein said open end of said second tube and said first second chamber outlet are substantially coaxial.

20. The separator of claim 16 wherein said second tube includes a plurality of ports communicating with the interior of said second tube.

\* \* \* \* \*